(12) United States Patent
Darko

(10) Patent No.: US 6,342,530 B1
(45) Date of Patent: Jan. 29, 2002

(54) COMPOSITION AND METHOD FOR PARENTERAL ADMINISTRATION OF IBUPROFEN D,L- OR L-LYSINE SALT

(75) Inventor: Laszlo Darko, Westport, CT (US)

(73) Assignee: Farmacon-Il, LLC, Westport, CT (US)

( * ) Notice: Subject to any disclaimer, the term of this patent is extended or adjusted under 35 U.S.C. 154(b) by 0 days.

(21) Appl. No.: 09/712,430

(22) Filed: Nov. 14, 2000

(51) Int. Cl.⁷ ............................................. A61K 31/195
(52) U.S. Cl. ...................................................... 514/561
(58) Field of Search ................................. 514/520, 561

(56) References Cited

U.S. PATENT DOCUMENTS

| | | |
|---|---|---|
| 4,279,926 A | 7/1981 | Bruzzese |
| 4,593,044 A | 6/1986 | Metz |
| 4,994,604 A | 2/1991 | Tung |
| 5,472,954 A * | 12/1995 | Loftsson ...................... 514/48 |
| 5,510,385 A | 4/1996 | Stroppolo |
| 5,622,990 A | 4/1997 | Katdare |
| 5,895,789 A | 4/1999 | Gentile |

* cited by examiner

*Primary Examiner*—James H. Reamer
(74) *Attorney, Agent, or Firm*—Herbert Dubno; Jonathan Myers

(57) ABSTRACT

Pharmaceutical compositions are disclosed suitable for parenteral administration having anti-inflammatory, analgesic, and anti-pyretic properties, which consist of a therapeutically effective amount of d,l or l-lysine salt of R,S or S-ibuprofen as active ingredient dissolved in sterile water to form a solution in the absence of an inert atmosphere and either substantially free or absolutely free of any excipient, organic solvent, buffer, acid, base, salt other than the active ingredient and capable of storage in the absence of an inert atmosphere. Also disclosed are methods employing the new compositions in the treatment of pain and inflammation, in reducing fever and in treating patent ductus arterious or intraventricular hemorrhage in prematurely born neonates.

20 Claims, No Drawings

COMPOSITION AND METHOD FOR PARENTERAL ADMINISTRATION OF IBUPROFEN D,L- OR L-LYSINE SALT

FIELD OF THE INVENTION

This invention relates to pharmaceutical compositions of the d,l- or l-lysine salt of R,S or S-ibuprofen having analgesic, anti-inflammatory and anti-pyretic activity. The invention further relates to a method of treating pain or inflammation or of reducing fever by parenterally administering the pharmaceutical compositions to a mammalian subject in need of such treatment, especially to a patient who is a neonate or who is suffering from kidney disease. The invention further relates to R,S or S-ibuprofen-d,l or l-lysine especially formulated for babies born at 28 to 32 weeks of gestational age to treat patent ductus arterious (PA) and to treat or prevent intraventricular hemorrhage (IVH). The invention also relates to a process for preparing the pharmaceutical compositions of the d,l- or l-lysine salt of R,S or S-ibuprofen.

BACKGROUND OF THE INVENTION

Lysine salts of ibuprofen having anti-inflammatory and analgesic activity are known in the art. See U.S. Pat. No. 4,994,604 to Tung et al. The Tung et al patent is specifically directed to the formation and resolution of ibuprofen-(S)-lysine into the (S)-ibuprofen-(S)-lysine and (R)-ibuprofen-(S)-lysine salts. There is no mention or suggestion of preparing compositions containing either optical isomer suitable for parenteral administration.

U.S. Pat. Nos. 5,510,385 and 5,622,990 also disclose lysine salts of ibuprofen. Both patents disclose that the lysine salts of ibuprofen are in a solid form suitable for oral administration such as tablets, caplets, powders and granulates. Once again there is no suggestion of forming a lysine salt of ibuprofen in a solution suitable for parenteral administration.

U.S. Pat. No. 4,279,926 is directed to pharmaceutical compositions containing among the salts of phenylalkanoic acids, the D,L and L lysine salts of ibuprofen. Compositions are prepared which are suitable for parenteral administration and include sterile aqueous or non-aqueous solutions, suspensions, or emulsions. The only aqueous composition suitable for parenteral administration disclosed in this patent contains 3 ml of 95% aqueous ethanol and 500 mg of ibuprofen. Such a system with its ethanol content would be not at all suitable to administer to a patient who is a neonate or a patient who suffers from kidney disease.

U.S. Pat. No. 5,895,789 is directed to an improvement in the invention disclosed in U.S. Pat. No. 4,279,926. According to this patent the compositions suitable for parenteral administration, containing an alkylammonium salt of a 2-arylpropionic acid, including ibuprofen, include an aqueous solution having an osmolarity between 270 and 310 mOsm/kg and a pH in the range of 7.0 to 7.5. The solution is free of preservatives and of supporting substances and is prepared and kept in an inert gas atmosphere and away from light. According to the reference the use of an inert gas during the preparation of the compositions and their subsequent storage enables reaching a degree of stability sufficient to avoid the need for adding preservatives and co-solvents for example alcohols or glycols for preventing the progressive yellowing of the solution. It is noted that while this patent mentions ibuprofen among the 2-arylpropionic acids and mentions the d,l lysine and l lysine salts as specific alkylammonium salts of the 2-arylpropionic acids, there is no express mention and certainly no example of any lysine salt of ibuprofen.

Because U.S. Pat. No. 5,895,789 requires that the pH of the aqueous solution containing the alkylammonium salts of the 2-arylpropionic acids to remain between 7.0 and 8.5 and to have an osmolarity of between 270 and 310 mOsm/kg, the compositions are buffered with a $C_3$ to $C_5$ di- or tricarboxylic acid or an alkali or alkaline earth metal salt thereof selected from the group consisting of tartronic, malic, tartaric and citric acids. The preferred buffer is a citric acid/sodium hydroxide and/or sodium citrate buffer. It is also required that the compositions according to this patent be packaged in dark glass containers opaque to light radiation.

One of the problems often associated with premature neonates (babies born at 28 to 32 weeks of gestational age) is patent ductus arterious (PDA). The drug presently used to treat this indication is indomethacin. A major side effect of indomethacin after administration to neonates is renal failure. Indomethacin is effective in the treatment of PDA because indomethacin inhibits the biosynthesis of prostaglandin.

OBJECTS OF THE INVENTION

It is an object of the invention to prepare stable pharmaceutical compositions of the d,l or l-lysine salt of R,S or S-ibuprofen having anti-inflammatory, analgesic and anti-pyretic activity and which are suitable for parenteral administration, need not be prepared and stored under an inert gas atmosphere and need not be packaged in dark glass containers opaque to light radiation.

It is a further object of the invention to obtain stable pharmaceutical compositions of the d,l- or l-lysine salt of R,S or S-ibuprofen having anti-inflammatory, analgesic, and anti-pyretic activity that are safe for administration to any patient in need of said treatment, including neonates and patients suffering from a kidney disorder.

It is a further object of the invention to provide stable pharmaceutical compositions that may be administered to neonates to treat patent ductus arterious (PDA) and intraventricular hemorrhage (IVH) to inhibit the biosynthesis of prostaglandin and that are free of the side effects caused by administration of indomethacin.

SUMMARY OF THE INVENTION

We have found that pharmaceutical compositions which satisfy all of these requirements consist of a therapeutically effective amount of the d,l- or l-lysine salt of R,S or S-ibuprofen as active ingredient dissolved in sterile water to form a solution in the absence of an inert atmosphere and either free or substantially free of any excipient, organic solvent, buffer, acid, base, salt other than the active ingredient and capable of storage in the absence of an inert atmosphere.

We have also found a method of treating pain or inflammation or of reducing fever in a mammalian subject by parenterally administering to said mammalian subject a therapeutically effective amount of the pharmaceutical composition described in the preceding paragraph. Such a mammalian subject may include human patients, including neonates who may have been born prematurely and patients suffering from a kidney disorder, including nephritis, nephrosis, cancer of the kidney and kidney failure.

A preferred feature of the present invention is the administration of the present composition to premature neonates (especially neonates born at 28 to 32 weeks of gestational age). The compositions of the present invention may be administered to these very small patients to block the biosynthesis of prostaglandin and at the same time the patients are free of the side effects associated with indomethacin, e.g. renal failure, the inhibitor of prostaglandin biosynthesis known in the art for treating this condition.

According to the present invention the d,l- or l-lysine salts of R,S or S ibuprofen are prepared without any addition of sodium chloride thus making the product safer for infants or other patients whose renal function, especially electrolyte elimination, is already compromised. The dosage form of this solution is 10 mg of R,S or S ibuprofen d,l or l lysinate (calculated on the basis of the ibuprofen not the salt) per ml of water. Preferably 1 to 2 ml of the solution are administered by injection to a patient as a daily dosage.

The new pharmaceutical compositions of the present invention may be prepared alternatively as follows:
(a) dissolving the d,l- or l-lysine salt of R,S or S ibuprofen in sterile water to form a solution in the absence of an inert atmosphere and free or substantially free of any excipient, organic solvent, buffer, acid, base, salt other than the active ingredient and capable of storage in the absence of an inert atmosphere; or
(b) dissolving d,l- or l-lysine and R,S or S ibuprofen in sterile water to form in situ a solution of the l-lysine salt of R,S ibuprofen in the absence of an inert atmosphere and absolutely free or substantially free of any excipient, organic solvent, buffer, acid, base, salt other than the active ingredient and capable of storage in the absence of an inert atmosphere.

The compositions according to the present invention are prepared either without the addition of any excipient, organic solvent, buffer, acid, base, salt other than the active ingredient or with the addition of only a minor amount (no more than 1% by weight) of the excipient, organic solvent, buffer, acid, base, salt other than the active ingredient to either control the solution osmolarity or the solution pH. For instance aqueous solutions prepared according to the present invention contain no more than 1% sodium chloride and preferably no more than 0.75% sodium chloride. Thus there is either no addition or substantially no addition of NaCl, HCL, citric acid or any of the other buffering agents or osmolarity adjusting compounds that have been included in the prior art pharmaceutical compositions. Such compositions which avoid sodium are especially suitable for administration to neonates and to kidney patients who cannot readily remove sodium from their systems.

The preferred concentration of the d,l or l ibuprofen lysine suitable for parenteral administration expressed in terms of percentage by weight with respect to the sterile water is between 1 to 20% by weight or strength. The preferred route of parenteral administration is through injection. Preferably the injection is intravenous, intramuscular or subcutaneous.

The preferred concentration of the ibuprofen lysinate is 1 to 20 mg, preferably 10 mg per ml of sterile aqueous solution calculated on the basis of the ibuprofen content and not on the basis of the lysinate salt irrespective as to whether the solution is substantially free or absolutely free of any excipient, organic solvent, buffer, acid, base, salt other than the active ingredient. When preparing the compositions that are substantially free, the percentage of salt (pharmaceutically acceptable) in the solution is either identical to that of an isotonic solution or less than that of an isotonic solution. Sodium chloride is the preferred pharmaceutically acceptable salt and is preferably added to the ibuprofen lysinate in a percentage ranging from 0.75 to 1.0. When preparing solutions that are absolutely free the product is especially safe for infants or other patients whose renal function, especially electrolyte elimination, is already compromised.

A preferred strength of the product in terms of the ibuprofen content of the sterile aqueous solution ranges between 1 and 20%, preferably 5.95 to 10%.

The following examples show preparation of the new compositions according to the present invention:

EXAMPLE 1

352 g of R,S ibuprofen d,l-lysine are dissolved in sterile distilled water without any excipient to adjust osmolarity, organic solvent, buffer, acid, base, or salt other than d,l-lysine in the absence of an inert atmosphere. Under mixing the desired sterile solution is formed. A quantity of the sterile solution is placed in an ampoule and is ready for use.

EXAMPLE 2

234 g of R,S ibuprofen and 166 g of l-lysine are each dissolved in sterile distilled water without any excipient to adjust osmolarity, organic solvent, buffer, acid, base, or salt other than l-lysine in the absence of an inert atmosphere. Under vigorous mixing a solution of the desired R,S ibuprofen d,l-lysine sterile solution is formed. A quantity of the sterile solution is placed in an ampoule and is ready for use.

EXAMPLE 3

The same procedures and reaction conditions as employed in Example 2 are employed here except that a small amount of sodium chloride is added so that the resulting aqueous solution contains 0.75% by weight sodium chloride. The resulting aqueous solution contains 10 mg of R,S ibuprofen d,l-lysine per ml of solution.

Examples Directed to Manufacturing and Packaging the Product

EXAMPLE 4

Formulation Substantially Free of any Excipient, Organic Solvent, Buffer, Acid, Base, Salt Other Than the Active Ingredient 54.0 kg of water for injection (WFI) are added to a vessel whose weight has been determined. The temperature is determined and if required, the temperature is raised or lowered to a range between 15° C. and 30° C. This temperature range is maintained throughout the formulation process. Mixing is begun at 600 to 800 RPM. 504.24 g of sodium chloride UMP/E are added. The weighed vessel which contained sodium chloride is rinsed with 3 increments of WFI. The rinses are added to the vessel and the contents of the vessel are mixed for another ten minutes.

By visual determination a check is made to learn whether all of the sodium chloride has been dissolved. Once the dissolution is completed, 650 g of ibuprofen lysinate are then added to the vessel. The weighed containers which once held ibuprofen lysinate are rinsed with 3 increments of WFI. All rinses are added to the vessel and mixed for another 10 minutes. Then a check is made to determine if all of the isoprufen lysinate has been dissolved. Once dissolved a 10 ml sample is withdrawn and its pH measured against a standardized pH meter. The pH is adjusted to 7.2 to 7.6 by adding 0.1N sodium hydroxide or 0.1N hydrochloric acid solution. The amount of WFI needed to achieve the final qs weight is determined. The WFI is added to qs until the final vessel and solution weight is reached. The solution is then mixed for 10 minutes. Once again 10 ml of the sample are withdrawn and the pH is measured. The pH is adjusted once again to a level of 7.2 to 7.6 with a target of 7.4. Then 20 ml of sample are taken from the vessel for quality control. In addition two 20 ml bioburden samples are submitted to environmental control. Mixing is then discontinued, the vessel is closed, and the contents are transferred to the filtering area. After filtering, the solution is transferred to an aseptic filling area. The concentration of the solution is 10 mg/ml based on the weight of the ibuprofen only, not the weight of the ibuprofen lysinate.

Through filters, the solution is transferred to the filling vessel. Sterile vials are filled from the filling vessel and each vial is provided with a sterilized, dry stopper. The vials are then closed with a sterile dried stopper. The vials are sterilized at 123° C. at a cycle time of 22 minutes and have a D/Value of 1.14.

EXAMPLE 5

Formulation absolutely free of any excipient, organic solvent, buffer, acid, base, salt other than the active ingredient 54.0 kg of water for injection (WFI) are added to a vessel whose weight has been determined. The temperature is determined and if required, the temperature is raised or lowered to a range between 15° C. and 30° C. This temperature range is maintained throughout the formulation process. Mixing is begun at 600 to 800 RPM. 650 g of ibuprofen lysinate are then added to the vessel. The weighed containers which once held ibuprofen lysinate are rinsed with 3 increments of WFI. All rinses are added to the vessel and mixed for another 10 minutes. Then a check is made to determine if all of the ibuprofen lysinate has been dissolved. Once dissolved a 10 ml sample is withdrawn and its pH measured against a standardized pH meter. The pH is determined to be 6.9. The amount of WFI needed to achieve the final qs weight is determined. The WFI is added to qs until the final vessel and solution weight is reached. The solution is then mixed for 10 minutes. Then 20 ml of sample are taken from the vessel for quality control. In addition two 20 ml bioburden samples are submitted to environmental control. Mixing is then discontinued, the vessel is closed, and the contents are transferred to the filtering area. After filtering, the solution is transferred to an aseptic filling area. The concentration of the solution is 10 mg/ml based on the weight of the ibuprofen only, not the weight of the ibuprofen lysinate.

Through filters, the solution is transferred to the filling vessel. Sterile vials are filled from the filling vessel and each vial is provided with a sterilized, dry stopper. The vials are then closed with a sterile dried stopper. The vials are sterilized at 123° C. at a cycle time of 22 minutes and have a D/Value of 1.14.

The following data in the table have been obtained for the composition according to Example 4. The data show that the composition has excellent storage stability over a period of over two years. The solution over that time period remains colorless, the pH remains constant, the assay remains constant, the levels of impurities remain low, the compositions remain sterile and there is no sign of particulates.

TABLE 1

Summary Sheet

| Product | Ibuprofen Lysinate Injection | Container | Wheaton 2702 B33 BA, 2 cc, 13 mm, flint tubing type I vial |
| --- | --- | --- | --- |
| Lot Number | 927-41-45822 | Closure | West 4416/50 V-35, 13 mm, plug, minimum silicone |
| Dosage | 2 ml/vial, 10 mg/mL | Raw Material | Ibuprofen L-Lysinate |
| | | Raw Material Manufacturer | Central Research Institute for Chemistry |

| Temp (° C.) | Parameter | Limits | Assay Orient | Dates 02/24/1998 Initial | 05/14/1998 1 Month | 06/12/1998 2 Month | 07/20/1998 3 Month |
| --- | --- | --- | --- | --- | --- | --- | --- |
| 25/60 % RH | Appearance | Clear, colorless solution essentially free from visible contaminants | UP | MR JLR-02 p137 | | | MR DXW-03 p40 |
| 25/60 % RH | Appearance | Clear, colorless solution essentially free from visible contaminants | INV | N/A | | | MR |
| 25/60 % RH | pH | 6.5 to 8.5 on a pooled sample | UP | 7.5 JLR-02 p137 | | | 7.3 DXW-03 p41 |
| 25/60 % RH | pH | 6.5 to 8.5 on a pooled sample | INV | N/A | | | 7.3 DXW-03 p41 |
| 25/60 % RH | Assay | 90.0% to 110.0% of the labeled amount | UP | 103.8% JLR-02 p146 | | | 105.2% DXW-03 p40 |

| Temp (° C.) | 10/09/1998 6 Month | 12/30/1998 9 Month | 03/22/1999 12 Month | 10/14/1999 18 Month | 04/25/2000 24 Month | 30 Month | 36 Month |
| --- | --- | --- | --- | --- | --- | --- | --- |
| 25/60 % RH | MR PAS-07 p44 | MR JJL-02 p39 | MR JJL-03 p12 | MR DLB-19 p139 | MR FLS-11 p47 | | |
| 25/60 % RH | MR PAS-07 p44 | MR JJL-02 p39 | MR JJL-03 p12 | MR DLB-19 p139 | MR FLS-11 p47 | | |
| 25/60 % RH | 7.3 PAS-07 p45 | 7.3 JJL-02 p39 | 7.3 JJL-03 p12 | 7.3 DLB-19 p139 | 7.3 FLS-11 p47 | | |
| 25/60 % RH | 7.4 PAS-07 p45 | 7.3 JJL-02 p39 | 7.3 JJL-03 p12 | 7.4 DLB-19 p139 | 7.3 FLS-11 p47 | | |
| 25/60 | 100.2% | 104.8% | 102.7% | 103.5% | 100.7% | | |

TABLE 1-continued

Summary Sheet

| % RH | PAS-07 p48 | JJL-02 p165 | JJL-03 p15 | DLB-19 p142 | FLS-11 p52 |
|------|------------|-------------|------------|-------------|------------|

N/A = Test not required for test interval
NMT = Not More Than
MR = Meet Requirements
Vials stored at RT prior to putting them on station
*= Initial testing performed on upright vials

TABLE 2

Summary Sheet

| Product | Ibuprofen Lysinate Injection | Container | Wheaton 2702 B33 BA, 2 cc, 13 mm, flint tubing type I vial |
|---|---|---|---|
| Lot Number | 927-41-45822 | Closure | West 4416/50 V-35, 13 mm, plug, minimum silicone |
| Dosage | 2 ml/vial, 10 mg/mL | Raw Material | Ibuprofen L-Lysinate |
| | | Raw Material Manufacturer | Central Research Institute for Chemistry |

| Temp (° C.) | Parameter | Limits | Assay Orient | Dates 02/24/1998 Initial | 05/14/1998 1 Month | 06/12/1998 2 Month | 07/20/1998 3 Month |
|---|---|---|---|---|---|---|---|
| 25/60 % RH | Assay | 90.0% to 110.0% of the labeled amount | INV | N/A | | | 105.0% DXW-03 p40 |
| 25/60 % RH | Impurities | Individual Impurity: NMT 1.0% | UP | 0.03% JLR-02 p148 | | | 0.06% DXW-03 p120 |
| 25/60 % RH | Impurities | Individual Impurity: NMT 1.0% | INV | N/A | | | 0.04% DXW-03 p121 |
| 25/60 % RH | Impurities | Total Impurity: NMT 2.0% | UP | 0.05% JLR-02 p148 | | | 0.1% DXW-03 p120 |
| 25/60 % RH | Impurities | Total Impurity: NMT 2.0% | INV | N/A | | | 0.01% DXW-03 p121 |

| Temp (° C.) | 10/09/1998 6 Month | 12/30/1998 9 Month | 03/22/1999 12 Month | 10/14/1999 18 Month | 04/25/2000 24 Month | 30 Month | 36 Month |
|---|---|---|---|---|---|---|---|
| 25/60 % RH | 100.2% PAS-07 p48 | 104.2% JJL-02 p165 | 102.5% JJL-03 p15 | 100.4% DLB-19 p142 | 100.6% FLS-11 p52 | | |
| 25/60 % RH | 0.02% PAS-07 p51 | 0.02% JJL-02 p80 | 0.02% JJL-03 p60 | 0.05% HLA-06 p167 | 0.02% FLS-11 p63 | | |
| 25/60 % RH | 0.02% PAS-07 p51 | 0.02% JJL-02 p80 | 0.02% JJL-03 p60 | 0.03% HLA-06 p168 | 0.02% FLS-11 p65 | | |
| 25/60 % RH | 0.08% PAS-07 p51 | 0.09% JJL-02 p80 | 0.1% JJL-03 p60 | 0.1% HLA-06 p167 | 0.2% FLS-11 p63 | | |
| 25/60 % RH | 0.08% PAS-07 p51 | 0.09% JJL-02 p80 | 0.1% JJL-03 p60 | 0.1% HLA-06 p168 | 0.1% FLS-11 p65 | | |

N/A = Test not required for test interval
NMT = Not More Than
MR = Meet Requirements
Vials stored at RT prior to putting them on station
*= Initial testing performed on upright vials

TABLE 3

Summary Sheet

| Product | Ibuprofen Lysinate Injection | Container | Wheaton 2702 B33 BA, 2 cc, 13 mm, flint tubing type I vial |
|---|---|---|---|
| Lot Number | 927-41-45822 | Closure | West 4416/50 V-35, 13 mm, plug, minimum silicone |
| Dosage | 2 ml/vial, 10 mg/mL | Raw Material | Ibuprofen L-Lysinate |
| | | Raw Material Manufacturer | Central Research Institute for Chemistry |

TABLE 3-continued

Summary Sheet

| Temp (° C.) | Parameter | Limits | Assay Dates Orient | 02/24/1998 Initial | 05/14/1998 1 Month | 06/12/1998 2 Month | 07/20/1998 3 Month |
|---|---|---|---|---|---|---|---|
| 25/60 % RH | Particulate Matter (HIAC) | NMT 6,000/10 um | UP | 38 H980122 PC | | | N/A |
| 25/60 % RH | Particulate Matter (HIAC) | NMT 6,000/10 um | INV | N/A | | | N/A |
| 25/60 % RH | Particulate Matter (HIAC) | NMT 600/25 um | UP | 0 H980122 PC | | | N/A |
| 25/60 % RH | Particulate Matter (HIAC) | NMT 600/25 um | INV | N/A | | | N/A |
| 25/60 % RH | Sterility | Sterile | INV | Sterile* S980152 F | | | N/A |

| Temp (° C.) | 10/09/1998 6 Month | 12/30/1998 9 Month | 03/22/1999 12 Month | 10/14/1999 18 Month | 04/25/2000 24 Month | 30 Month | 36 Month |
|---|---|---|---|---|---|---|---|
| 25/60 % RH | N/A | N/A | 34 H990299 C | N/A | 46 H 000457 PC | | |
| 25/60 % RH | N/A | N/A | 146 H990299 C | N/A | 78 H 000457 PC | | |
| 25/60 % RH | N/A | N/A | 0.4 H990299 C | N/A | 4 H 000457 PC | | |
| 25/60 % RH | N/A | N/A | 1.2 H990299 C | N/A | 6 H 000457 PC | | |
| 25/60 % RH | N/A | N/A LF | Sterile S990358 | N/A | Awaits Results | | |

N/A = Test not required for test interval
NMT = Not More Than
MR = Meet Requirements
Vials stored at RT prior to putting them on station
*= Initial testing performed on upright vials

TABLE 4

Summary Sheet

| Product | Ibuprofen Lysinate Injection | Container | Wheaton 2702 B33 BA, 2 cc, 13 mm, flint tubing type I vial |
|---|---|---|---|
| Lot Number | 927-41-45822 | Closure | West 4416/50 V-35, 13 mm, plug, minimum silicone |
| Dosage | 2 ml/vial, 10 mg/mL | Raw Material | Ibuprofen L-Lysinate |
| | | Raw Material Manufacturer | Central Research Institute for Chemistry |

| Temp (° C.) | Parameter | Limits | Assay Dates Orient | 02/24/1998 Initial | 05/14/1998 1 Month | 06/12/1998 2 Month | 07/20/1998 3 Month |
|---|---|---|---|---|---|---|---|
| 25/60 % RH | Bacterial Endotoxins | Contains NMT 0.5 USP EU/mg | INV | <0.1667* PLAL980 166 QCL | | | N/A |
| 40/75 % RH | Appearance | Clear, colorless solution essentially free from visible contaminants | UP | MR JLR-02 p137 | MR CMS-01 p134 | MR PAS-05 p182 | MR DXW-03 p40 |
| 40/75 % RH | Appearance | Clear, colorless solution essentially free from visible contaminants | INV | N/A | MR CMS-01 p134 | MR PAS-05 p182 | MR DXW-03 p40 |
| 40/75 % RH | pH | 6.5 to 8.5 on a pooled sample | UP | 7.5 JLR-02 p137 | 7.3 CMS-01 p135 | 7.3 PAS-05 p182 | 7.2 DXW-03 p41 |

| Temp (° C.) | 10/09/1998 6 Month | 12/30/1998 9 Month | 03/22/1999 12 Month | 10/14/1999 18 Month | 04/25/2000 24 Month | 30 Month | 36 Month |
|---|---|---|---|---|---|---|---|
| 25/60 % RH | N/A | N/A | N/A | N/A | <0.1667 PLAL 000682 QCL | | |

TABLE 4-continued

Summary Sheet

| | | |
|---|---|---|
| 40/75 % RH | MR | PAS-07 p44 |
| 40/75 % RH | MR | PAS-07 p44 |
| 40/75 % RH | 7.1 | PAS-07 p45 |

N/A = Test not required for test interval
NMT = Not More Than
MR = Meet Requirements
Vials stored at RT prior to putting them on station
*= Initial testing performed on upright vials

TABLE 5

Summary Sheet

| Product | Ibuprofen Lysinate Injection | | Container | Wheaton 2702 B33 BA, 2 cc, 13 mm, flint tubing type I vial | | | |
|---|---|---|---|---|---|---|---|
| Lot Number | 927-41-45822 | | Closure | West 4416/50 V-35, 13 mm, plug, minimum silicone | | | |
| Dosage | 2 ml/vial, 10 mg/mL | | Raw Material | Ibuprofen L-Lysinate | | | |
| | | | Raw Material Manufacturer | Central Research Institute for Chemistry | | | |
| Temp (° C.) | Parameter | Limits | Assay Dates Orient | 02/24/1998 Initial | 05/14/1998 1 Month | 06/12/1998 2 Month | 07/20/1998 3 Month |
| 40/75 % RH | pH | 6.5 to 8.5 on a pooled sample | INV | N/A | 7.4 CMS-01 p135 | 7.3 PAS-05 p182 | 7.3 DXW-03 p41 |
| 40/75 % RH | Assay | 90.0% to 110.0% of the labeled amount | UP | 103.8% JLR-02 p146 | 99.4% CMS-01 p138 | 99.4% PAS-05 p185 | 104.8% DXW-03 p46 |
| 40/75 % RH | Assay | 90.0% to 110.0% of the labeled amount | INV | N/A JLR-02 p148 | 99.3% CMS-01 p140 | 99.2% PAS-05 p188 | 105.0% DXW-03 p123 |
| 40/75 % RH | Impurities | Individual Impurity: NMT 1.0% | UP | 0.03% JLR-02 p148 | 0.02% CMS-01 p140 | 0.03% PAS-05 p188 | 0.07% DXW-03 p123 |
| 40/75 % RH | Impurities | Individual Impurity: NMT 1.0% | INV | N/A | 0.02% CMS-01 p139 | 0.02% PAS-05 p188 | 0.06% DXW-03 p125 |

| Temp (° C.) | 10/09/1998 6 Month | 12/30/1998 9 Month | 03/22/1999 12 Month | 10/14/1999 18 Month | 04/25/2000 24 Month | 30 Month | 36 Month |
|---|---|---|---|---|---|---|---|
| 40/75 % RH | 7.2 PAS-07 p45 | | | | | | |
| 40/75 % RH | 99.2% PAS-07 p48 | | | | | | |
| 40/75 % RH | 99.3% PAS-07 p48 | | | | | | |
| 40/75 % RH | 0.1% PAS-07 p57 | | | | | | |
| 40/75 % RH | 0.07% PAS-07 p58 | | | | | | |

N/A = Test not required for test interval
NMT = Not More Than
MR = Meet Requirements
Vials stored at RT prior to putting them on station
*= Initial testing performed on upright vials

TABLE 6

Summary Sheet

| Product | Ibuprofen Lysinate Injection | Container | Wheaton 2702 B33 BA, 2 cc, 13 mm, flint tubing type I vial |
|---|---|---|---|
| Lot Number | 927-41-45822 | Closure | West 4416/50 V-35, 13 mm, plug, minimum silicone |
| Dosage | 2 ml/vial, 10 mg/mL | Raw Material | Ibuprofen L-Lysinate |
| | | Raw Material Manufacturer | Central Research Institute for Chemistry |

| Temp (° C.) | Parameter | Limits | Orient | Assay Dates Initial 02/24/1998 | 05/14/1998 1 Month | 06/12/1998 2 Month | 07/20/1998 3 Month |
|---|---|---|---|---|---|---|---|
| 40/75 % RH | Impurities | Total Impurity: NMT 2.0% | UP | 0.05% JLR-02 p148 | 0.06% CMS-01 0.1% p140 | 0.1% PAS-05 p188 | 0.4% DXW-03 p123 |
| 40/75 % RH | Impurities | Total Impurity: NMT 2.0% | INV | N/A | 0.05% CMS-01 p139 | 0.1% PAS-05 p188 | 0.3% DXW-03 p125 |
| 40/75 % RH | Particulate Matter (HIAC) | NMT 6,000/10 um | UP | 38 H980122 PC | N/A | N/A | N/A |
| 40/75 % RH | Particulate Matter (HIAC) | NMT 6,000/10 um | INV | N/A | N/A | N/A | N/A |
| 40/75 % RH | Particulate Matter (HIAC) | NMT 600/25 um | UP | 0 H980122 PC | N/A | N/A | N/A |

| Temp (° C.) | 10/09/1998 6 Month | 12/30/1998 9 Month | 03/22/1999 12 Month | 10/14/1999 18 Month | 04/25/2000 24 Month | 30 Month | 36 Month |
|---|---|---|---|---|---|---|---|
| 40/75 % RH | 0.4% PAS-07 p57 | | | | | | |
| 40/75 % RH | 0.3% PAS-07 p58 | | | | | | |
| 40/75 % RH | 65 H980832 C | | | | | | |
| 40/75 % RH | 144 H9800832 C | | | | | | |
| 40/75 % RH | 3 H980832 C | | | | | | |

N/A = Test not required for test interval
NMT = Not More Than
MR = Meet Requirements
Vials stored at RT prior to putting them on station
*= Initial testing performed on upright vials

TABLE 7

Summary Sheet

| Product | Ibuprofen Lysinate Injection | Container | Wheaton 2702 B33 BA, 2 cc, 13 mm, flint tubing type I vial |
|---|---|---|---|
| Lot Number | 927-41-45822 | Closure | West 4416/50 V-35, 13 mm, plug, minimum silicone |
| Dosage | 2 ml/vial, 10 mg/mL | Raw Material | Ibuprofen L-Lysinate |
| | | Raw Material Manufacturer | Central Research Institute for Chemistry |

| Temp (° C.) | Parameter | Limits | Orient | Assay Dates Initial 02/24/1998 | 05/14/1998 1 Month | 06/12/1998 2 Month | 07/20/1998 3 Month |
|---|---|---|---|---|---|---|---|
| 40/75 % RH | Particulate Matter (HIAC) | NMT 600/25 um | INV | N/A | N/A | N/A | N/A |

TABLE 7-continued

Summary Sheet

| Temp (° C.) | 10/09/1998 6 Month | 12/30/1998 9 Month | 03/22/1999 12 Month | 10/14/1999 18 Month | 04/25/2000 24 Month | 30 Month | 36 Month |
|---|---|---|---|---|---|---|---|
| 40/75 % RH | 2 H980832 C | | | | | | |

N/A = Test not required for test interval
NMT = Not More Than
MR = Meet Requirements
Vials stored at RT prior to putting them on station
*= Initial testing performed on upright vials

What is claimed is:

1. A pharmaceutical composition in unit dosage form in a vial or ampoule having excellent storage stability over a period of 2 years and suitable for parenteral administration having anti-inflammatory, anti-pyretic and analgesic properties, which consists of a therapeutically effective amount of the d,l or l-lysine salt of R,S or S- ibuprofen as active ingredient dissolved in sterile water to form a solution in the absence of an inert atmosphere and substantially free of any excipient, organic solvent, buffer, acid, base, salt other than the active ingredient and capable of storage in the absence of an inert atmosphere.

2. A method of treating pain or inflammation or of reducing fever in a mammalian subject which comprises the step of parenterally administering to said mammalian subject, a therapeutically effective amount of the pharmaceutical composition defined in claim 1.

3. The method of treating pain or inflammation or of reducing fever defined in claim 2 wherein the mammalian subject is a human patient.

4. The method of treating pain or inflammation or of reducing fever defined in claim 3 wherein the human patient is a premature neonate.

5. The method of treating pain or inflammation or of reducing fever defined in claim 3 wherein the human patient suffers from kidney disease.

6. The method of treating pain or inflammation or of reducing fever defined in claim 2 wherein the pharmaceutical composition is administered by injection.

7. The method of treating pain or inflammation or of reducing fever defined in claim 6 wherein the injection is intravenous, intramuscular or subcutaneous injection.

8. A method of treating patent ductus arterious or intraventricular hemorrhage in a prematurely born neonate which comprises the step of parenterally administering to said prematurely born neonate, a therapeutically effective amount of the pharmaceutical composition defined in claim 1.

9. A method of preparing the pharmaceutical composition defined in claim 1 which comprises the steps of dissolving the d,l- or l-lysine salt of R,S or S-ibuprofen in sterile water to form a solution in the absence of an inert atmosphere and substantially free of any excipient, organic solvent, buffer, acid, base, salt other than the active ingredient and capable of storage in the absence of an inert atmosphere, adding the solution to a vial or ampoule, and closing the vial or ampoule.

10. A method of preparing the pharmaceutical composition defined in claim which comprises the step of dissolving d,l- or l-lysine and R,S or S-ibuprofen in sterile water to form in situ a solution of the d,l- or l-lysine salt of R,S or S-ibuprofen in the absence of an inert atmosphere and substantially free of any excipient, organic solvent, buffer, acid, base, salt other than the active ingredient and capable of storage in the absence of an inert atmosphere, adding the solution to a vial or ampoule, and closing the vial or ampoule.

11. A pharmaceutical composition in unit dosage form in a vial or ampoule shaving excellent storage stability over a period of 2 years and suitable for parenteral administration having anti-inflammatory, anti-pyretic and analgesic properties, which consists of a therapeutically effective amount of the d,l or l-lysine salt of R,S or S- ibuprofen as active ingredient dissolved in sterile water to form a solution in the absence of an inert atmosphere and absolutely free of any excipient, organic solvent, buffer, acid, base, salt other than the active ingredient and capable of storage in the absence of an inert atmosphere.

12. A method of treating pain or inflammation or of reducing fever in a mammalian subject which comprises the step of parenterally administering to said mammalian subject, a therapeutically effective amount of the pharmaceutical composition defined in claim 11.

13. The method of treating pain or inflammation or of reducing fever defined in claim 12 wherein the mammalian subject is a human patient.

14. The method of treating pain or inflammation or of reducing fever defined in claim 13 wherein the human patient is a premature neonate.

15. The method of treating pain or inflammation or of reducing fever defined in claim 13 wherein the human patient suffers from kidney disease.

16. The method of treating pain or inflammation or of reducing fever defined in claim 12 wherein the pharmaceutical composition is administered by injection.

17. The method of treating pain or inflammation or of reducing fever defined in claim 16 wherein the injection is intravenous, intramuscular or subcutaneous injection.

18. A method of treating patent ductus arterious or intraventricular hemorrhage in a prematurely born neonate which comprises the step of parenterally administering to said prematurely born neonate, a therapeutically effective amount of the pharmaceutical composition defined in claim 11.

19. A method of preparing the pharmaceutical composition defined in claim 11 which comprises the steps of dissolving the d,l- or l-lysine salt of R,S or S-ibuprofen in sterile water to form a solution in the absence of an inert atmosphere and absolutely free of any excipient, organic solvent, buffer, acid, base, salt other than the active ingredient and capable of storage in the absence of an inert atmosphere, adding the solution to a vial or ampoule, and closing the vial or ampoule.

20. A method of preparing the pharmaceutical composition defined in claim 11 which comprises the steps of dissolving d,l- or l-lysine and R,S or S-ibuprofen in sterile water to form in situ a solution of the d,l- or l-lysine salt of R,S or S-ibuprofen in the absence of an inert atmosphere and absolutely free of any excipient, organic solvent, buffer, acid, base, salt other than the active ingredient and capable of storage in the absence of an inert atmosphere, adding the solution to a vial or ampoule, and closing the vial or ampoule.

* * * * *